US00PP35990P2

(12) United States Plant Patent
Hansen

(10) Patent No.: US PP35,990 P2
(45) Date of Patent: Jul. 9, 2024

(54) ***HIBISCUS* PLANT NAMED 'Marshmallow Moon'**

(50) Latin Name: ***Hibiscus* hybrid (L.)**
Varietal Denomination: Marshmallow Moon

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/445,450

(22) Filed: Aug. 22, 2023

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
See application file for complete search history.

*Primary Examiner* — Susan McCormick Ewoldt
*Assistant Examiner* — Zachariah Allan Kay

(57) ABSTRACT

A new and distinct cultivar of winter-hardy, herbaceous, perennial, hybrid *Hibiscus* plant named 'Marshmallow Moon' comprising a compact, round-mounded habit of multiple, well-branched, basal stems producing flowers beginning in late July to early August and continuing for at least eight weeks. Flowers have overlapping petals of white without a reddish eye. The foliage is primarily three-lobed and dark-green-colored. The new plant is useful in the landscape as a specimen or in mass.

2 Drawing Sheets

Botanical classification: *Hibiscus* hybrid (L.).
Variety denomination: 'Marshmallow Moon'.

STATEMENT REGARDING PRIOR DISCLOSURES UNDER 37 CFR 1.77(B)(6)

The first offer for sale of *Hibiscus* 'Marshmallow Moon' was on Feb. 2, 2023, by Walters Gardens, Inc. The first brief disclosure with a limited description and photograph was on Feb. 1, 2022, on a website maintained by Walters Gardens, Inc. Walters Gardens, Inc. followed this with a short description and photograph in their "Walters Gardens 2023-2024 Catalog" first distributed on May 19, 2023. Walters Gardens, Inc. obtained the new plant and all information relating thereto, from the inventor. No plants of *Hibiscus* 'Marshmallow Moon' have been sold, anywhere in the world by any name, nor has any disclosure of the new plant been made more than one year prior to the filing date of this application, and such sale or disclosure within one year was either derived directly or indirectly from the inventor.

BACKGROUND AND ORIGIN OF THE PLANT

The present invention relates to the new and distinct hardy, herbaceous, *Hibiscus* plant, *Hibiscus* 'Marshmallow Moon', hybridized under the direction of the inventor on Aug. 8, 2018, at a wholesale perennial nursery in Zeeland, Michigan. The new plant is a self-pollination of the unreleased, proprietary hybrid known as 18-205-2 (not patented). During the trial process, the new plant was assigned the breeder code labeled 19-243-3. The parent has a complex mixture of species in them, believed to be comprising the species: *moscheutos, grandiflora, lastocarpos*, and *coccineus*.

*Hibiscus* 'Marshmallow Moon' was first asexually propagated in the late summer of 2020 by sterile shoot-tip tissue culture and later by shoot-tip cuttings at the same nursery in Zeeland, MI. The resultant asexually propagated plants have found both propagation methods to be stable and true to type in successive generations of asexual reproduction.

BRIEF SUMMARY OF THE PLANT

*Hibiscus* 'Marshmallow Moon' differs from its parents as well as all other hardy herbaceous *Hibiscus* known to the applicant in many traits. The most similar *Hibiscus* known to the applicant are: 'Blue River II' (not patented), LUNA™ 'White' (not patented), 'Old Yella' U.S. Plant Pat. No. 13,630, 'New Old Yella' U.S. Plant Pat. No. 23,698, 'French Vanilla' U.S. Plant Pat. No. 33,181, and 'Cookies and Cream' U.S. Plant Pate. No. 35,736.

'Blue River II' has a larger and more upright open habit, the flowers are held more near the top of the plant, are flatter with less overlapping of petals, and the foliage is lighter green and ovate to weakly tri-lobed. LUNA™ 'White' is an F1 hybrid cultivar and has a slightly smaller habit, lighter green, ovate foliage, and the flowers have a reddish eye. 'Old Yella', 'New Old Yella', and 'French Vanilla' all have creamy yellow flowers with a reddish eye. 'Old Yella' has a slightly larger habit with ovate to weakly tri-lobed foliage. 'French Vanilla' has stiffer stems and foliage that is tri-lobed to penta-lobed, and blushed strongly with burgundy, and begins flowering later. 'Cookies and Cream' has a slightly shorter habit with chocolate-colored foliage and flowers with multiple flowers per node in succession in the distal part of the peduncle.

The parent has a taller habit, the flowers have longer pedicels with a more drooping habit with less overlapping and less texture in the petals.

*Hibiscus* 'Marshmallow Moon' is a unique hardy herbaceous *Hibiscus* with the following combined traits:

1. Winter-hardy compact perennial with a rounded mounded habit of multiple, well-branched, basal stems;

2. Many rotate flowers with overlapping petals of white without a reddish eye;
3. Flowering beginning in late July to early August and continuing for at least eight weeks;
4. Three-lobed foliage of dark-green color.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source, and direction may cause the appearance of minor variations in color.

DETAILED BOTANICAL DESCRIPTION

Figure 1:
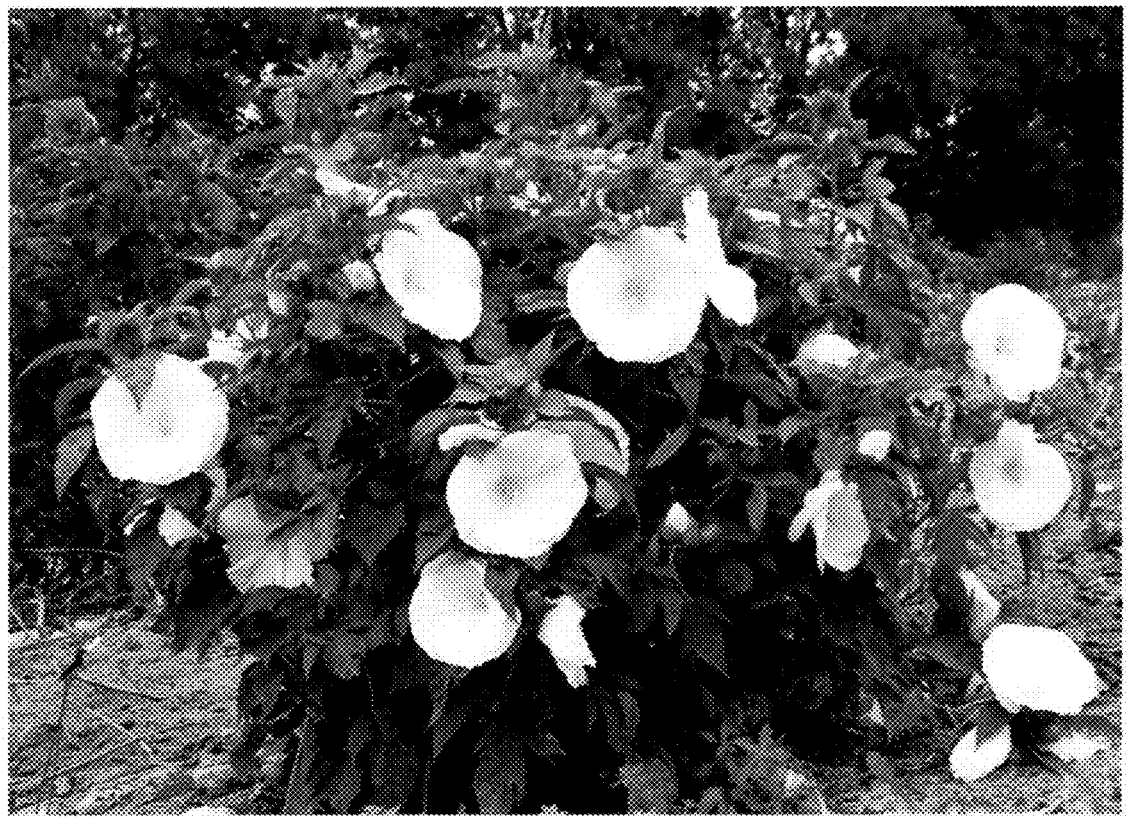
FIG. 1 shows a two-year-old plant in full flower in a research field.
Figure 2:
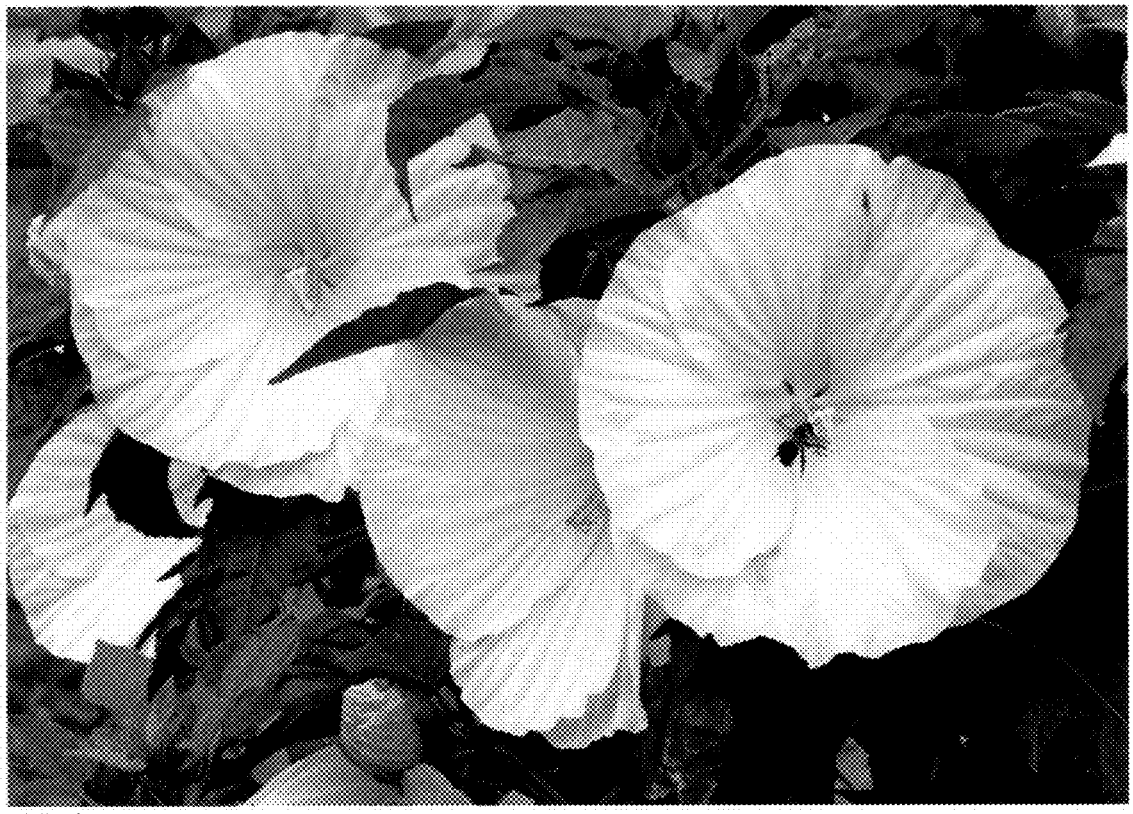
FIG. 2 shows a close-up of the flowers and bud of a two-year-old plant.

The following descriptions and color references are based on the 2015 edition of The Royal Horticultural Society Colour Chart except where common dictionary terms are used. The new plant, *Hibiscus* 'Marshmallow Moon', has not been observed in all possible environments. The phenotype may vary slightly with different environmental conditions, such as temperature, light, fertility, moisture and maturity levels, but without any change in the genotype. The following observations and size descriptions are of a four-year-old plant in the loamy-sand, open-field full-sun display garden of a nursery in Zeeland, MI with supplemental fertilizer and water as needed. The plants are of natural habit and were not treated with plant growth regulators, nor were they pinched at any time in the growth year.

Parentage: The parent is the unreleased, non-patented, proprietary *Hibiscus* known by the breeder code 18-205-2;

Propagation:

*Method*.—Shoot tip cuttings and sterile shoot-tip plant tissue culture division.

*Time to initiate roots from tissue culture*.—About two weeks.

*Rooting habit*.—Normal, branching, developing thick to about 2 cm diameter, fleshy; root color creamy yellow nearest RHS 161D depending on soil type.

*Crop time*.—Under normal summer growing conditions 12 to 16 weeks to flower in a four-liter container from cutting. Plant vigor is very good.

Plant description:

*Plant habit*.—Hardy herbaceous perennial with about 33 thick, upright to outright, heavily-branched stems producing an upright spreading mound to about 108 cm tall and about 137 cm wide; flowering in upper two-thirds of plant with up to about 20 flowers per distal main unbranched stem, up to 9 flowers per branch, and to about 50 flowers per stem.

*Stem*.—Cylindrical, glabrous, glaucous; to about 145 cm tall and about 16 mm diameter at base, average about 100 cm tall and about 12 mm diameter at base; branched.

*Stem color*.—Between RHS 146D and RHS 148C, without anthocyanins.

*Branches*.—To 17 per stem, average about 9 per stem; cylindrical, glabrous, glaucous; to about 57 cm long and 8 mm diameter at base, smaller distally.

*Branch color*.—Between RHS 146D and RHS 148C, without anthocyanins.

*Internode*.—About 17 nodes per stem below single flowers and 29 single flowers; average 42 nodes per stem; internode length about 2.5 cm of unpinched plant.

*Internode color*.—Same as surrounding stem.

Foliage description: Primarily tri-lobed with occasional penta-lobed, with lobes of varying lengths; alternate; coarsely and irregularly dentate; apex and side lobes acute; base cordate to rounded; micro-puberulent and matte both abaxial and adaxial; moderately incised, with incisions from 2 cm to 5 cm deep;

Leaf blade size: To about 17.5 cm long and about 17 cm across, average blade size 14 cm long and 12.5 cm wide; no fragrance detected;

*Foliage color*.—Young expanding leaves — adaxial nearest RHS 137B, abaxial nearest RHS 147B; mature leaves — adaxial between RHS 139A and RHS NN137A, abaxial nearest RHS 147B.

*Veins*.—Palmate; micro-puberulent adaxial and abaxial; flat adaxial, costate abaxial.

*Vein color*.—Adaxial between RHS 146D and RHS 145C proximally and distally nearest RHS 146B; abaxial veins primary veins between RHS 146D and RHS 145C proximally, and distally nearest RHS 148B, and secondary veins nearest RHS NN137B.

*Petioles*.—Mostly cylindrical, proximally slightly applanate on adaxial side near base; micro-puberulent; to about 7.5 cm long and 5 mm across at base, average size about 5 cm long and 4 mm wide at base.

*Petiole color*.—Adaxial nearest RHS 146C; abaxial nearest RHS 146D.

Flower description: Complete; perfect; actinomorphic; rotate; solitary; mostly outward facing; slightly cupped; one flower per node in distal peduncle;

Flower size: To about 16.5 cm across natural spread, 7.5 cm deep, and 20 cm wide if flattened; decreasing distally and later in the season;

*Buds one day prior to anthesis*.—Ellipsoidal with broadly acute apex and truncate base; sepals adpressed to petals; to about 4.5 cm long and about 3.5 cm diameter near middle.

*Bud color one day prior to anthesis*.—Exposed petal color nearest RHS 4D and calyx between RHS 144A and RHS 146D.

*Epicalyx*.—Average about 12 per flower; linear; margin entire and micro-ciliolate; dull and micro-puberulent abaxial and adaxial; sharply acute apex and truncate base, arcuate upwards near apex; to about 33 mm long and about 4 mm wide at base.

*Epicalyx color*.—Adaxial nearest RHS 146A and abaxial nearest RHS 137A.

*Calyx*.—Campanulate, forming star-shaped hypanthium; to about 27 mm deep and 90 mm wide at apices.

*Sepals*.—Five; ovate; acute apex; margin entire, edentate; abaxial micro-puberulent and matte, adaxial glabrous and matte; about 49 mm long, about 26 mm wide at fusion, basal 19 mm fused.

*Sepal color*.—Adaxial proximal portion nearest RHS 147C, distal portion nearest RHS 147B with veins nearest RHS 145C; abaxial nearest RHS 137B.

*Inflorescence*.—Up to 50 per main stem including branches without pinching.

*Flower lastingness*.—Persist for one to two days; effective for at least 10 weeks beginning late July to early August.

*Flower fragrance*.—No detectable fragrance.

*Petals*.—Typically, five, rarely six to eight; glabrous adaxial and abaxial; adaxial 1 cm proximal eye zone lustrous, remaining distal adaxial portion, and entire abaxial matte; adnate to the androecium to form a column, imbricate to about 110% overlapping at widest part (petals overlapping both petals on either side, so three petals are stacked about 10%); undulation moderate; palmately veined, primary veins moderately impressed on adaxial and moderately costate abaxial; surface mostly flat, leading petal edge occasionally folded; apex rounded with distinct basal claw and limb; margins entire, edentate.

*Petal size*.—Average about 12.2 cm across and about 8.2 cm long, claw base about 8 mm across.

*Petal color*.—Adaxial proximal 1 cm between RHS NN155B and RHS NN155C, distal portion between RHS NN155B and RHS NN155C; abaxial between RHS NN155C, and RHS NN155B.

Gynoecium: Single; partially enclosed in column;

*Column*.—Glabrous and lustrous; about 33 mm long and about 10 mm across at base; with pistil exserted about 20 mm.

*Column color*.—Nearest RHS NN155C.

*Style*.—To about 43 mm long, penta-furcate in about distal 7 mm, branch diameter about 1 mm; micro-puberulent in distal branched region, glabrous below and in column; color nearest RHS NN155A in exposed portion, and RHS NN155C portion enclosed in column.

*Stigma*.—Typically, five; flattened globose, puberulent, about 3 mm in diameter and 1.5 mm tall; color in nearest RHS 4D.

*Ovary*.—Superior; inverted conical, longitudinally grooved in undulated pattern; acute apex, and truncate base; about 9 mm across at base and about 9 mm tall; color between RHS 145A and RHS 145B.

Androecium: Attached to column;

*Filaments*.—Numerous, about 100, attached starting about 8 mm from base to the apex of column; to about 3 mm long, about 0.2 mm diameter; color nearest RHS N155C.

*Anthers*.—Flattened reniform; dorsifixed; about 1 mm across, 2 mm long, and about 1 mm thick; color nearest RHS 4D.

*Pollen*.—Abundant, globose, less than 0.1mm across; color nearest RHS 11D.

Pedicel: Cylindrical, micro-puberulent in distal and proximal portions; length from base of sepal to abscission point about 3 cm long, from abscission point to stem node about 2.5 cm long; about 3.5 mm wide; longer on early flowers and decreasing in distal flowers;

Pedicel color: Nearest RHS 146D proximal and distal the abscission point;

Peduncle: Cylindrical, glabrous, glaucous; flowering portion to about 37 cm tall and about 9 mm diameter just below single flowers, average about 34 cm tall and about 8 mm diameter at base;

Peduncle color: Between RHS 146D and RHS 148C, without anthocyanins;

Fruit and seeds: Not yet observed;

Resistance: *Hibiscus* 'Marshmallow Moon' has not displayed any pest and disease resistance beyond that typical of hardy perennial *Hibiscus*. The plant grows best with plenty of moisture. Hardiness at least from USDA zone 4 through 9.

I claim:

1. A new cultivar of hardy herbaceous perennial *Hibiscus* hybrid plant named 'Marshmallow Moon' as herein illustrated and described.

* * * * *